(12) United States Patent
Gleason

(10) Patent No.: US 6,287,265 B1
(45) Date of Patent: Sep. 11, 2001

(54) BLOOD COLLECTION KIT

(76) Inventor: Cindy L. Gleason, USAHC BHR, Unit #23809 HQ, APO, AE (US), 09034

(*) Notice: Subject to any disclaimer, the term of this patent is extended or adjusted under 35 U.S.C. 154(b) by 0 days.

(21) Appl. No.: 09/436,408

(22) Filed: Nov. 9, 1999

Related U.S. Application Data

(60) Provisional application No. 60/140,958, filed on Jun. 23, 1999.

(51) Int. Cl.[7] .............................. A61B 5/00; B65D 81/00
(52) U.S. Cl. ............................................................ 600/573
(58) Field of Search .................................. 600/573, 575, 600/577, 579; 604/248, 539

(56) References Cited

U.S. PATENT DOCUMENTS

| | | |
|---|---|---|
| D. 271,421 | 11/1983 | Fetterman . |
| 3,157,201 | 11/1964 | Littmann . |
| 3,780,736 | 12/1973 | Chen . |
| 4,566,480 | 1/1986 | Parham . |
| 4,593,717 * | 6/1986 | Levasseur ........................... 604/248 |
| 4,608,050 | 8/1986 | Wright et al. . |
| 4,608,996 | 9/1986 | Brown . |
| 4,730,936 | 3/1988 | Thorjusen, Jr. . |
| 4,763,648 * | 8/1988 | Wyatt .................................. 600/575 |
| 4,838,855 * | 6/1989 | Lynn .................................... 600/577 |
| 4,981,140 * | 1/1991 | Wyatt .................................. 600/575 |
| 5,002,066 | 3/1991 | Simpson et al. . |
| 5,122,129 | 6/1992 | Olson et al. . |
| 5,221,271 * | 6/1993 | Nicholson et al. .................. 604/539 |
| 5,289,858 | 3/1994 | Grabenkort . |
| 5,417,673 * | 5/1995 | Gordon ............................... 604/539 |

* cited by examiner

Primary Examiner—John P. Lacyk
Assistant Examiner—Brian Szmal
(74) Attorney, Agent, or Firm—Banner & Witcoff, Ltd.

(57) ABSTRACT

A whole blood sampling kit for obtaining blood samples from a central line. The system is comprised of three syringes, a 4-way stopcock body, and a needle or blunt cannula access devise. The three syringes are a 1 cc heparinized syringe for blood sampling, an empty 3 cc blood and infusing fluid aspirating syringe, and a 3 cc flush filled syringe. The syringes are attached to three female ports on the top of the kit's stopcock. A lever on the kit's stopcock points to the female port and syringe it is on to. A needle or blunt cannula is attached to the male adapter on the bottom of the kit's stopcock. The access device connected to the male adapter has a locking system with a matching sample site. The whole kit, via the needle or blunt cannula, attaches to a central line's sample site for withdrawing blood.

16 Claims, 11 Drawing Sheets

- PRIOR ART -

- PRIOR ART -

- PRIOR ART -

- PRIOR ART -

- PRIOR ART -

- PRIOR ART -

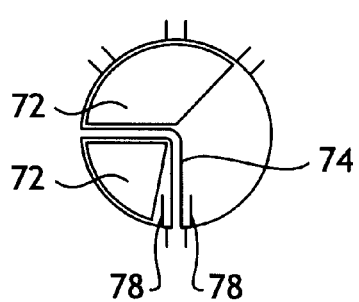
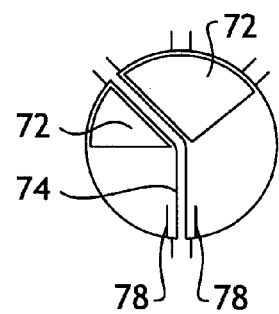
Fig. 11A
Fig. 11B
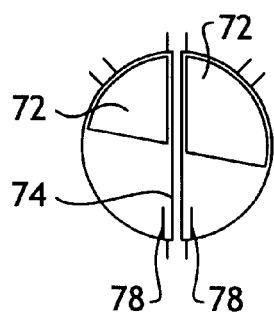
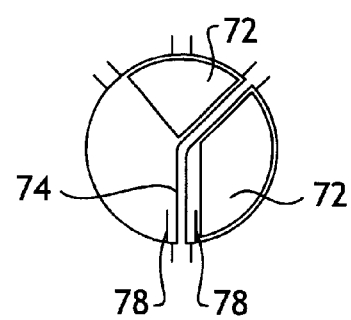
Fig. 11C
Fig. 11D

BLOOD COLLECTION KIT

This application claims the benefit of Provisional No. 60/140,958 filed Jun. 23, 1999.

FIELD OF INVENTION

This invention relates to arterial blood collection from arterial lines, specifically to an arterial blood collection kit designed for premature infants with an umbilical artery catheter.

BACKGROUND—DESCRIPTION OF PRIOR ART

In the United States umbilical artery catheters (UACs) are the central line of choice in a neonatal ICU for obtaining arterial blood gases. UACs are also used to monitor internal blood pressure through a transducer attached to the infusing fluids line. UACs are relatively easy to place in a newborn because the umbilical cord is freshly cut and the artery is easy to see. When a neonate is critically ill or premature, frequent arterial blood gases are needed to assess their respiratory status. When an infant is on a ventilator, the blood gas results are used to adjust the ventilator settings appropriately. UACs are only placed in infants needing frequent arterial blood gases, not just to get normal labs or monitor the infant's blood pressure.

A UAC line setup is shown in FIG. 1 and consists of the following: a UAC catheter 22 inserted into a neonate's umbilical artery, a stopcock 24 with a female port 66, an IV line for infusing fluids 26, and a transducer for monitoring blood pressure (not shown). The system through the catheter is filled with saline solution and heparin. Slow dripping of saline and heparin into the patient prevents clotting of blood in the catheter and therefore keeps the line open. The infusing fluids usually run at 0.5 cc–1 cc per hour in a neonate.

A currently used process for obtaining blood samples from the female port 66 on the stopcock is described below. Shift the stopcock off to infusing fluids (FIG. 1B); this opens the fluid path between the catheter and the syringe. Draw 0.5 cc–1.5 cc of blood into the empty 3 cc syringe 28 to clear the UAC of all infusing fluids and bring whole blood to the female port of the stopcock. Shift the stopcock off to all lines (FIG. 1C). Remove this syringe and keep it sterile. Place a 1cc heparinized syringe on the stopcock. Shift the stopcock off to the infusing fluids. Draw back on the 1cc syringe until a 0.1–0.3 cc sample is obtained. Shift the stopcock off to all lines. Remove the 1 cc syringe and replace the blood filled 3 cc syringe onto the stopcock. Shift the stopcock off to the infusing fluids. Aspirate on the syringe to remove any air that may be trapped, then give the blood back to the patient. Shift the stopcock off to all lines. Remove the 3cc syringe and place a 3 cc flush filled syringe onto the stopcock. Shift the stopcock off to the infusing fluids. Aspirate on the syringe to remove any air, then flush to clear the line of blood, usually 0.5–1 cc. Shift stopcock off to all lines. Remove the 3 cc flush syringe and place a sterile, empty 3 cc syringe on the stopcock. Shift the stopcock off to the syringe. Now the system is open again to the slow dripping of saline and heparin and ready for the next blood draw.

The foregoing procedure has obvious disadvantages. A large number of manipulative steps are required to carry out the procedure. More important are the many chances for contamination of the female port of the stopcock during the frequent switching of syringes. Neonates can die very quickly and suddenly from sepsis even in a neonatal intensive care setting. The syringe most likely to become contaminated is the first 3 cc syringe used to clear the line of infusing fluids prior to blood sampling. If this syringe becomes contaminated it must be thrown away along with the infant's blood. One may think that 5 0.5 cc–1.5 cc of blood is not that much, but in a 1 to 4 pound infant it is. The blood volume for a neonate is approximately 90 cc/kg* (or 41 cc/lb). For premature infants whose blood volume can be as little as 50 cc or less, anemia is commonly caused by blood draws.* Infants can go into shock if they lose ¼ or more of their blood volume. For example, a micro-premier weighing 500 grams (1 pound 2 ounces) would only have to lose about 11 cc or a little more than 2 teaspoons of blood to go into shock. Infants need the most blood samples taken when they are acutely ill. Arterial blood gases will be drawn every ½ hour to every 4 hours when an infant is on a ventilator. So, one can easily see how often an infant is exposed to contamination and the risk of blood loss.

When using the above procedure for blood sampling, one must be sure to shift the stopcock off to all lines before changing syringes or blood will run out of the open port. Obviously this would lead to more blood loss for the neonate.

An apparatus for drawing arterial blood samples and monitoring blood pressure has been introduced to neonatal intensive care, but seems to be designed with pediatrics or adults in mind. Please see FIG. 2.

The procedure for drawing from this apparatus is as follows. First make sure a 10 cc flush syringe 40 has 3–8 cc of flush solution in it. There can not be more than 8cc of flush in this syringe or there may not be room to draw back enough blood to clear the line for blood sampling. Shift stopcock 34 so it is off to the infusing fluids. Aspirate on syringe 40 until blood reaches a black line 38 on a tubing 36 to clear the line of infusing fluids and bring whole blood to an access port 30. Shift stopcock 34 so it is off to everything. Clean an access port 30 and introduce a shrouded needle with a 1 cc heparinized syringe into it. The shrouded needle locks onto the port Shift stopcock 34 so it is off to the infusing fluids. Withdraw 0.1–0.3 cc of blood into the 1 cc syringe and remove it from the sample portMove back to syringe 40 and flush the line to clear it of blood, up to 4 cc of flush is needed at times. Shift stopcock 34 off to syringe 40, as it is in FIG. 2, and the connection between the infusing fluids and the UAC is open again.

While this apparatus has greatly decreased the chance of contamination of the line, it has to also caused many new problems. It is very bulky and spread out. For this reason, many nurses will place an additional stopcock 24 on the line (as I did in FIG. 2) and continue drawing blood samples with the procedure described previously. Therefore, the apparatus is used only for transducing the blood pressure and the original contamination risks are still a factor.

Another significant drawback of the apparatus is 2.5 cc of blood has to be aspirated to reach the black line 38. This is compared to 0.5 cc–1.5 cc drawn off with the first procedure described. Also, more flush is needed to clear the line after blood sampling because the apparatus is so spread out. Although it is designed to require 1 cc of flush, the flush needed to clear the line of blood can be up to 4 cc. More blood drawn off and more flush needed to clear the line is very significant in premature babies. Premature infants and especially micro-premies are most critically ill and most prone to intracranial bleeds during the first few days of life. Intracranial bleeds can be caused by just positioning a premature infant wrong. More important in this instance, intracranial bleeds can be caused by sudden fluid shifts such as taking off or adding fluid to their system suddenly. Also during the first few days of life, when they are most critically ill, is when they need the most arterial blood draws to assess respiratory status.

When an infant needs a bolus of fluid, that fluid is given at 10 cc per kilogram over at least 20 minutes to protect their brain. For example, a 500 kilogram infant would receive a 5 cc bolus over at least 20 minutes. With the current apparatus 2.5 cc of fluid is drawn off the infant. Then that 2.5 cc plus 1 cc–4 cc of flush is added to the infant over a matter of seconds.

If more than the minimal amount of flush is used with a neonate, over a short period of time electrolyte imbalances can occur. Electrolyte imbalances can cause many problems such as cardiac dysrythmias, bronchopulmonary dysplasia, seizures, etc.

With a 10 cc syringe it is difficult to assess exactly how much flush is used. The larger the syringe the less accurate the readings. In the neonatal ICU, input and output are recorded to the tenths and sometimes hundredths (0.0–0.00).

Also, some neonatal ICU's standard operating procedure states a clean flush should be used with each blood drawing procedure from a UAC. Obviously this is not happening with this apparatus. Or the system is being opened each time risking contamination to change the flush syringe at connection 41. Also, so much flush is used the flush syringe needs changed frequently.

Another risk with this apparatus is air in the line. For example, the person performing the blood draw happens to place the sample syringe on the sample port prior to clearing the line of infusing fluids. The result is air being drawn through the syringe and into the line as a syringe 40 is aspirated on to bring whole blood to the sampling site. This would lead to changing the whole system out, or drawing the air (and blood and saline) out into several syringes until the line is cleared of air, and then flushing the line with a new flush filled syringe. Either response chosen to clear the air in the line leads to a considerable amount of the infant's blood being thrown away.

If an additional stopcock is added to the apparatus, as I said some nurses will do, the stopcock's controls can be positioned incorrectly leading to flush filled blood in line 36 being drawn into the blood sampling syringe. This leads to skewed lab results and more blood being drawn to repeat the labs.

The above apparatus has the blood collecting unit permanently incorporated into the fluid line with the blood pressure transducer. If the apparatus is used on a peripheral arterial line of a neonate, only the transducer is used from the system to monitor blood pressure. The blood drawing part of the apparatus can not be used and is wasted on a peripheral arterial line in a neonate because blood can not be aspirated out. If blood is aspirated out of a peripheral arterial line in a neonate arterial damage can occur, possibly leading to the permanent loss of a hand or foot.

Neither of the current procedures used for blood sampling are appropriate for the neonatal intensive care.

SUMMARY

The present invention is a compact, disposable kit that fits on any female port of a central or arterial line for collecting blood specimens. This kit is especially designed for neonates but could also be used on pediatric and adult patients.

OBJECTS AND ADVANTAGES

The objective of the present invention is to provide an apparatus for taking blood samples which is designed especially for neonates in a neonatal intensive care setting. Accordingly, several objects and advantages of the present invention are:

(a) to provide a blood drawing apparatus that essentially eliminates the risk of contamination of the patient.

(b) to provide a blood drawing apparatus with decreased and easy to understand steps.

(c) to provide a blood drawing apparatus in which the stopcocks and syringes to be manipulated are in close proximity to one another.

(d) to provide a process for attaching and removing the apparatus to the sampling port whereas the blood can not flow out of the sampling port even if the arterial line stopcock is left open to the port and the catheter.

(e) to provide a blood drawing apparatus that nurses will find worthwhile to use rather than the old process of switching many syringes on an open port and risking contamination or reconfiguring current apparatuses.

(f) to provide a blood drawing apparatus that needs minimal aspiration of blood and infusing fluids to bring the patient's blood to the sampling port.

(g) to provide a blood drawing apparatus that uses the minimal amount of flush needed to clear the stopcock and catheter of blood after a sample is taken.

h) to provide a blood drawing apparatus with the smallest syringe possible as the flush syringe so as to know exactly how much flush is used.

(i) to provide a sterile blood drawing apparatus which uses fresh flush with each blood draw and is removed from the line and discarded after use.

(j) to provide a blood drawing apparatus which eliminates the risk of air being introduced into the arterial line.

(k) to provide a blood drawing apparatus and process which can be fit onto any female port of an arterial line.

(l) to provide an apparatus which can be used for blood sampling if needed, but will not be wasted on a peripheral arterial line that can not be aspirated on in neonates.

(m) to provide an apparatus which can be used also to draw additional labs if needed without opening the system and compromising the sterility of the umbilical artery line.

(n) to provide three different blood drawing kits in separate sterile packages in order to provide an appropriate kdt for each blood drawing procedure anticipated.

The objective of the present invention is to provide a safer, simpler system for taking samples of blood from UACs wherein the chance for contaminating the patient is almost, if not entirely, eliminated. Further objects and advantages of this invention will become apparent from a consideration of the drawings and ensuing description.

DRAWING FIGURES

In the drawings, closely related figures have the same number but different alphabetical suffixes.

FIG. 9A shows the kit's stopcock off to all ports.

FIG. 9B shows the Kit's stopcock on to the blood sampling syringe.

FIG. 9C shows the kit's stopcock on to the 3 cc blood and infusing fluid aspirating syringe.

FIG. 9D shows the kit's stopcock on to the 3 cc flush syringe.

FIG. 9E is a top view of the inside of the blood collecting kit's stopcock.

FIG. 9F is a bottom view of the inside of the blood collecting kit's stopcock.

FIG. 10A shows the kit's stopcock off to all ports.

FIG. 10B shows the kit's stopcock on to the blood sampling syringe.

FIG. 10C shows the kit's stopcock on to the 3 cc blood and infusing fluid aspirating syringe.

FIG. 10D shows the kit's stopcock on to the flush syringe.

FIG. 10E is a top view of the inside of the blood collecting kit's stopcock.

FIG. 10F is a bottom view of the inside of the blood collecting kit's stopcock.

FIGS. 11A–11D show another embodiment of the inside of the blood collecting kit and its positions.

FIG. 11A shows the kit's stopcock off to all ports.

FIG. 11B shows the kit's stopcock on to the blood sampling syringe.

FIG. 11C shows the kit's stopcock on to the 3 cc blood and infusing fluid aspirating syringe.

FIG. 11D shows the kit's stopcock on to the flush syringe.

REFERENCE NUMERALS IN DRAWINGS

Figure 1:
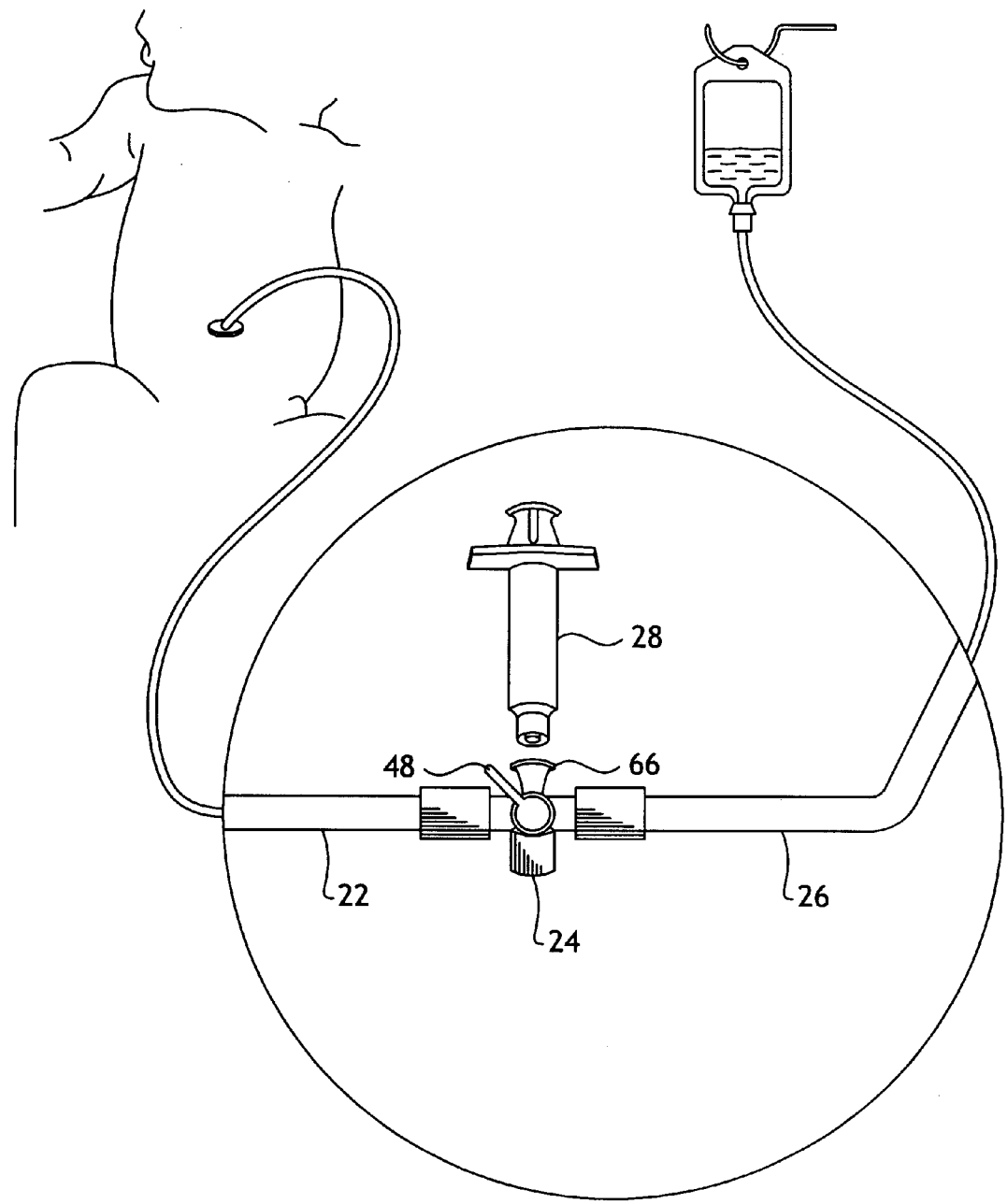
FIG. 1 shows the setup for the currently used process for obtaining a blood sample from an umbilical artery catheter.
Figure 1A:
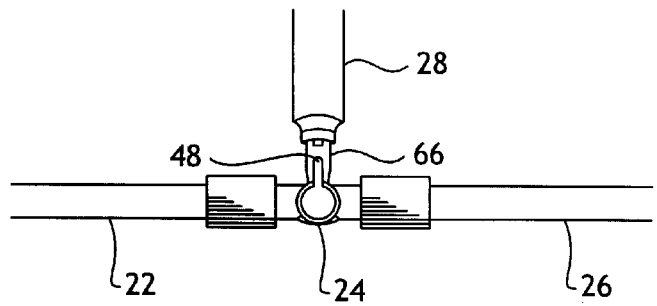
FIG. 1A shows the stopcock positioned off to the sampling port and syringe. Therefore, the fluids are infusing into the catheter.
Figure 1B:
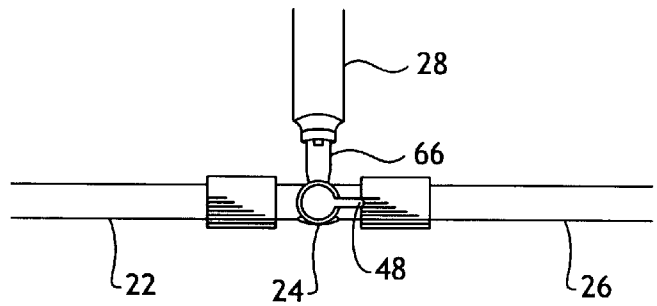
FIG. 1B shows the stopcock positioned off to the infusing fluids. The line is open between the catheter and the sampling port.
Figure 1C:
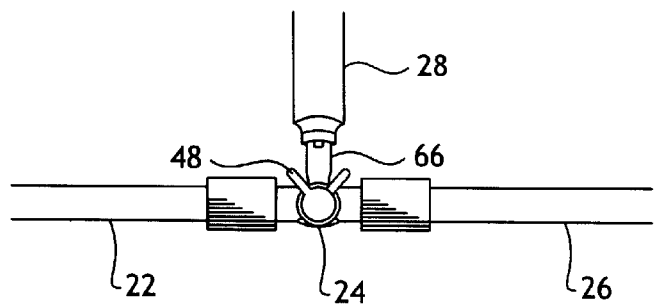
FIG. 1C shows two positions in which the stopcock is off to all ports.
Figure 2:
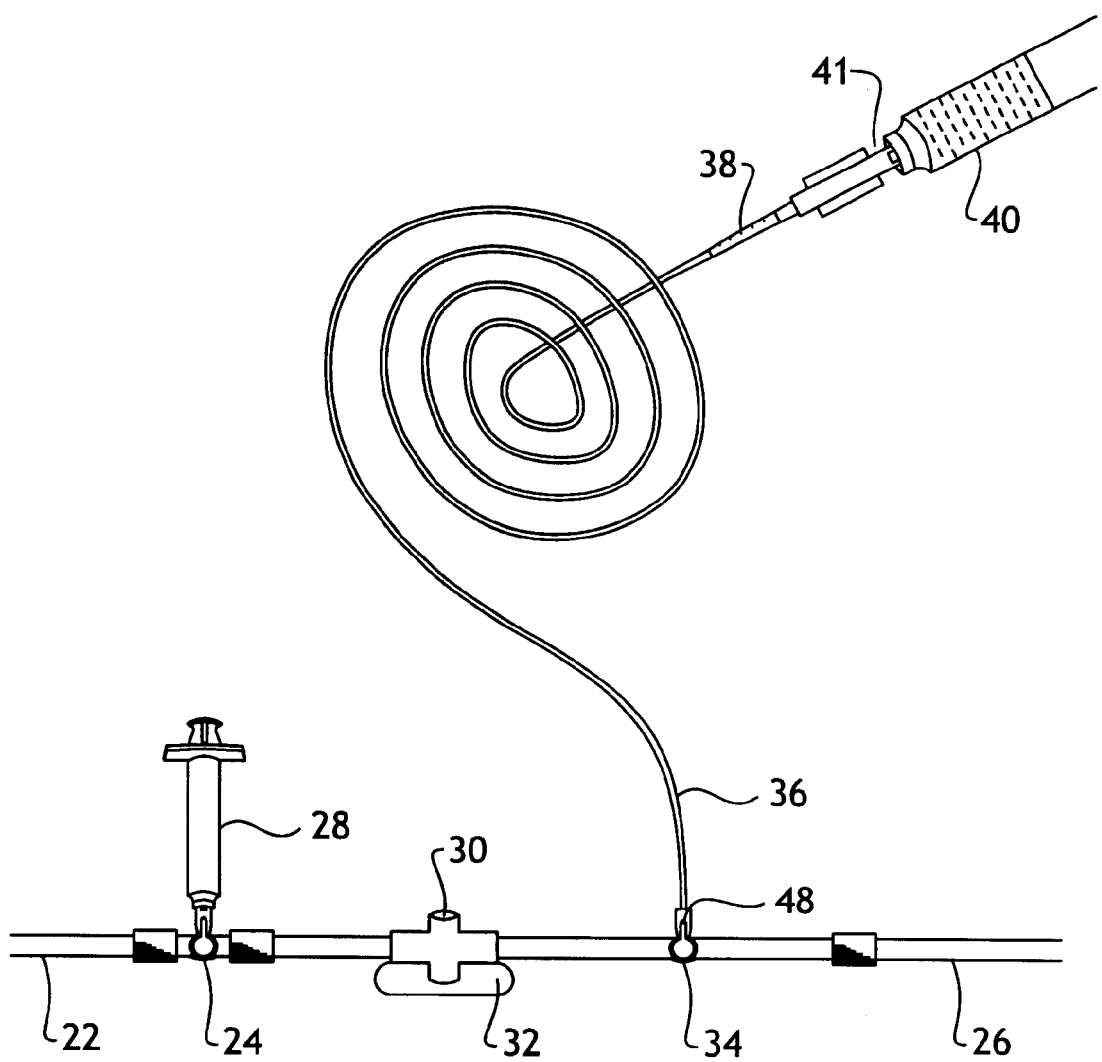
FIG. 2 shows a prior art apparatus currently used to draw blood from an arterial line.

| | |
|---|---|
| 22 umbilical artery catheter | 24 stopcock |
| 26 infusing fluids line | 28 empty 3 cc syringe |
| 30 access port | 32 stand |
| 34 stopcock permanently attached | 36 tubing to flush syringe |
| | 40 10 cc flush filled syringe |
| 38 1 inch black mark on tubing | 42A–42C female ports |
| 41 connection site | 46 4-way stopcock of kit |
| 44 male adapter | 50 1 cc heparinized syringe |

-continued

REFERENCE NUMERALS IN DRAWINGS

| | |
|---|---|
| 48 stopcock lever | 54 needle or blunt cannula |
| 52 flush filled 3 cc syringe | 56 sample site |
| 55 access device | 60 sealing cap |
| 58 sealing cap | 64 plastic shroud |
| 62 clip | 68 notch |
| 66 female port | 74 flexible tubing |
| 72 firm moveable plastic | (ex: Silastic) |
| 76 hollow passage | 78 plastic stops |

DESCRIPTION—FIGS. 3–7—PREFERRED EMBODIMENT

Figure 3:
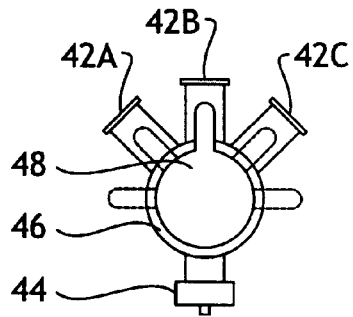
FIG. 3 shows the current main invention, the blood collecting kit.
Figure 3A:
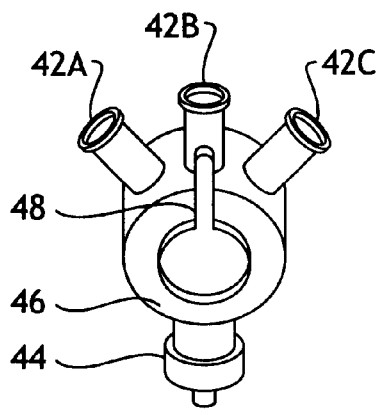
FIG. 3A shows a perspective view of the blood collecting kit.

FIG. 3 shows a front view of the main invention, the arterial blood collecting kit. I have shown this separate as it is the only equipment in the drawings that is not prior art that I know of.

The body of a blood collecting kit 46 is a stopcock with 3 female ports 42A–42C coming off the top at 20–30 degree angles from each other and a male adapter 44 coming out the middle bottom of the main body 46 directly in line with female port 42B. The body of the blood collecting kit's stopcock is the same size as standard prior art stopcocks. Female ports 42A–42C are for syringe connection for blood sampling. The syringes connected to the ports could be different sizes and attached in different order than is shown. But, for the neonatal intensive care, the smallest syringes possible should be used as shown. A lever 48 points to the female port stopcock 46 is on to and in connection with the male adapter. A male adapter 44 can be attached to any female port, access device, needle or blunt cannula.

Figure 4:
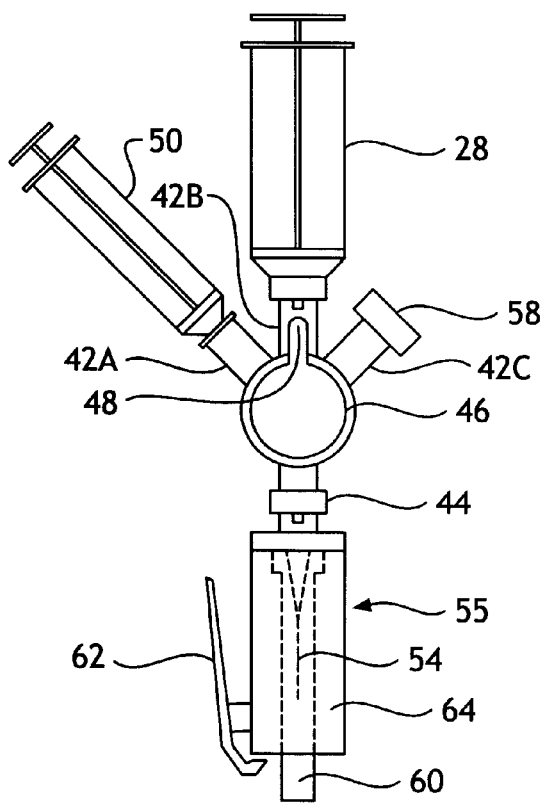
FIG. 4 shows how the arterial blood collecting kit would come packaged.

FIG. 4 shows the blood collecting kit as it would come in a sterile package. It would be important to package it like this with caps 58 and 60 in place to keep the ports sterile when the package is opened. Cap 58 will be replaced with a flush filled 3 cc syringe prior to attaching the kit to the sampling port. Cap 60 will be removed immediately before placing the kit onto a sample site. An access device 55 is attached to male adapter 44. A needle or blunt cannula 54 is in the access device for penetration through an access port. Plastic shroud 64 protects the needle or blunt cannula from becoming contaminated. The plastic shroud also protects staff from needle sticks. The needle or blunt cannula, shroud, and locking system make up an access device 55. There are several types of prior art locking access devices with matching ports. I have given only one example in the drawings. A locking devise on the needle or blunt cannula is important to keep the kit attached to the sample site during blood collection. Clip 62 is like ½ of a clothespin that locks the kit onto the sample site. A 1 cc heparinized syringe 50 and an empty 3 cc syringe 28 will already be attached to the kit. Having the kit come as preassembled as possible decreases the chance of contamination and makes the blood sampling procedure easier and faster. Also, the stopcock lever 48 will come pointed to female port 42. This means the fluid path is open on the kit between a syringe 28 and a male adapter 44. The empty 3 cc syringe connected to female port 42B is the first syringe to be manipulated during a blood drawing procedure using the blood collecting kit.

Figure 5:
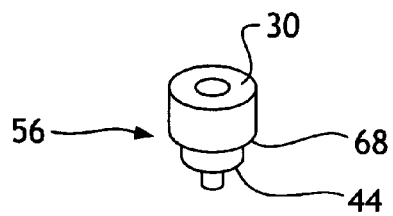
FIG. 5 shows a prior art sampling port.

FIG. 5 shows a prior art sample site 56. An access port 30 could be for needle or blunt cannula access. Some plugs in an access port 30 allow access by needle and blunt cannula. Most important, this sample site 56 has a locking system that matches the access device attached to the kit's male adapter 44. A notch 68 is where the clip of the access device locks onto the sample site. These sample sites come packaged separately. A sample site 56 is attached to the female port of the stopcock on the UAC line during initial setup of the UAC line and during line changes every 24 hours. Once the sample site is attached to the line it is not removed again until the whole line is changed out.

Figure 6:
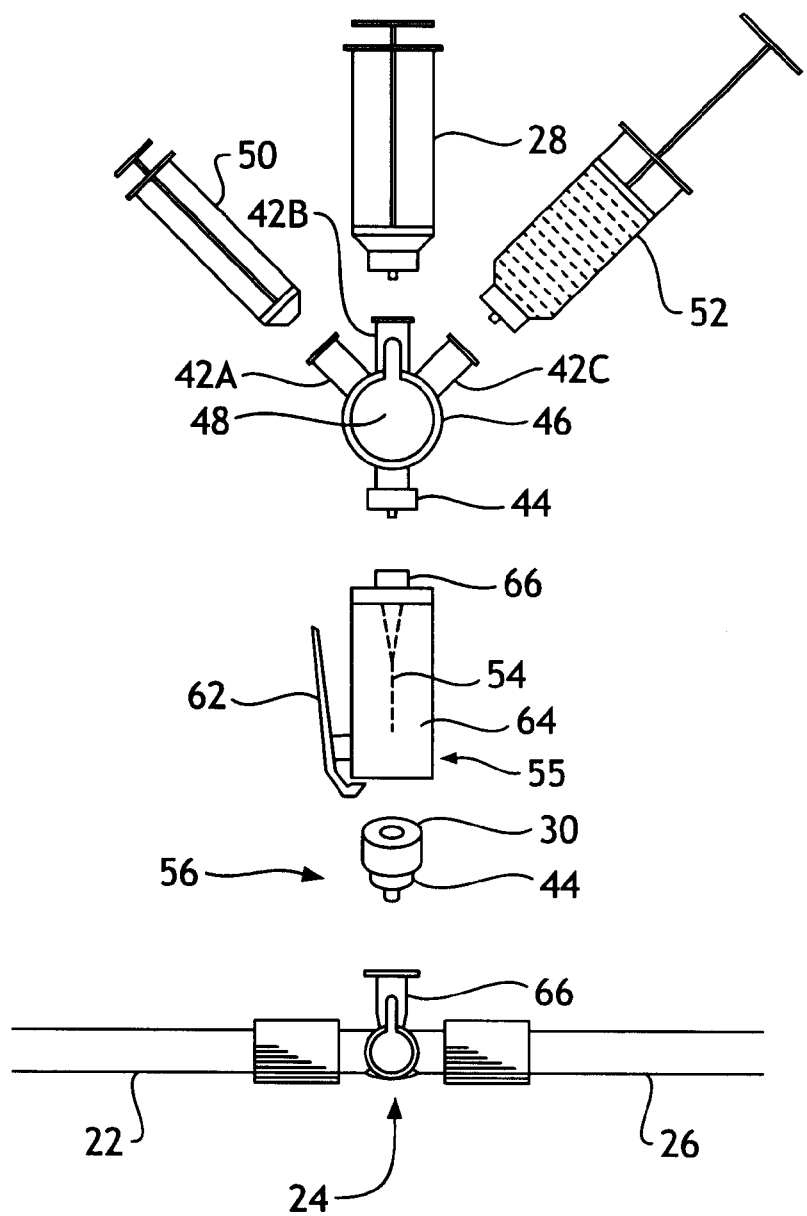
FIG. 6 shows how the prior art and the blood collecting kit would be fit together.

FIG. 6 shows how the parts of the blood collecting kit fit together with the sample site on the UAC line for blood sampling. A needle or blunt cannula 54 penetrates the access port and clip 62 locks onto the sample site. Stopcock lever 48 is positioned on to syringe 28 and ready for blood sampling. All the syringes, including the flush filled 3 cc syringe, are attached to the kit and ready for blood sampling.

Figure 7:
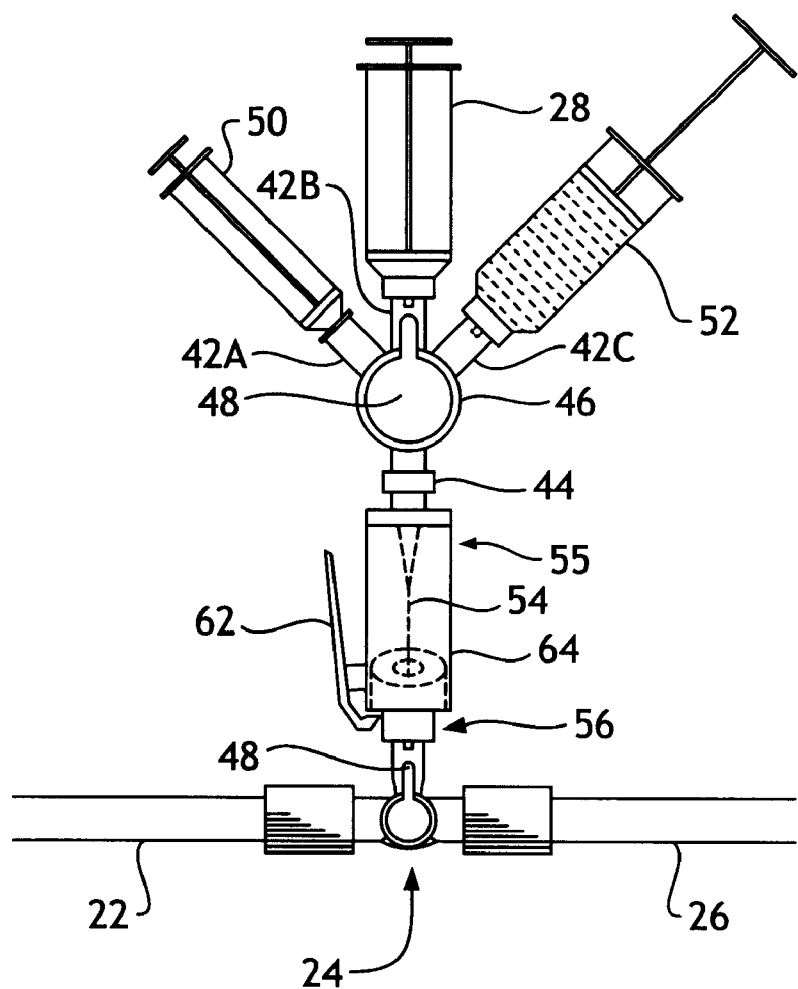
FIG. 7 shows the blood collecting kit attached to the female port on the prior art stopcock.

FIG. 7 shows the present invention as it is attached to the sample site and ready for the blood collection. Note the UAC line stopcock is off to the kit.

Operation and Advantage—FIG. 7

The blood sampling procedure with the blood collecting kit is quick and easy to understand. Clean an access port 30 of the sample site on the UAC line and attach a prepared blood collecting kit. Position the stopcock of the UAC line so it is off to the infusing fluids. Aspirate on an empty 3 cc syringe 28 until 0.5 cc–1.5 cc of blood and infusing fluids are in the syringe. Position lever 48 so it is on to the 1 cc heparinized syringe. Aspirate 0.1–0.3 cc blood for the blood sample. Position lever 48 back on to the 3 cc blood filled syringe 28 and give the blood back to the patient. Position lever 48 on to the 3 cc flush filled syringe and flush the line until it is clear of blood. Position the stopcock of the UAC line so it is off to the blood collecting kit and remove the kit from the sampling port.

From the foregoing, it can be seen that the manipulative steps are greatly reduced and the stopcocks and syringes being manipulated are in close proximity to one another. By placing the kit on a closed sample site the risk of contamination is essentially eliminated. Also, by having a closed sample site, blood can not flow out of the sample site no matter which position stopcock 24 is in when the kit is attached or removed. Not only does this save the neonate from losing blood, but it also protects staff from being exposed to the blood.

The only step to prepare the kit for blood sampling is to attach a flush filled syringe. Several kits could be prepared at one time and ready for use at the bedside. A flush syringe would have to be prepared anyway for the old process to be carried out. Also, a fresh, sterile flush is used with each blood draw as it should be.

Since the kit uses a 3 cc syringe as the flush syringe the amount of flush used can be more accurately recorded.

The kit adds only a small apparatus to the original arterial line. The needle or blunt cannula and the kit's stopcock would only hold about 0.24 cc of fluid. Therefore it requires much less blood to be aspirated to bring the whole blood to the sampling port compared to the prior art apparatus. Also, less flush is needed to clear the line after blood sampling compared to the spread out prior art apparatus. This is very significant in neonates, because intracranial bleeds can be caused by sudden shifts of fluids in their systems and by quick changes in their blood pressure.

There is no risk of air being introduced into the line because there is never even a possibility of communication between syringes.

This kit can be fit onto any female port of a central or arterial line. It is removed after the blood sampling and does not produce more clutter on a neonate's small bed.

The blood collecting kit is not wasted on a neonate's peripheral arterial line like the prior art apparatus. Because, an arterial line on a neonate can not be aspirated on, and the kit is not a permanent unit of the line with the blood pressure transducer.

Figure 8:
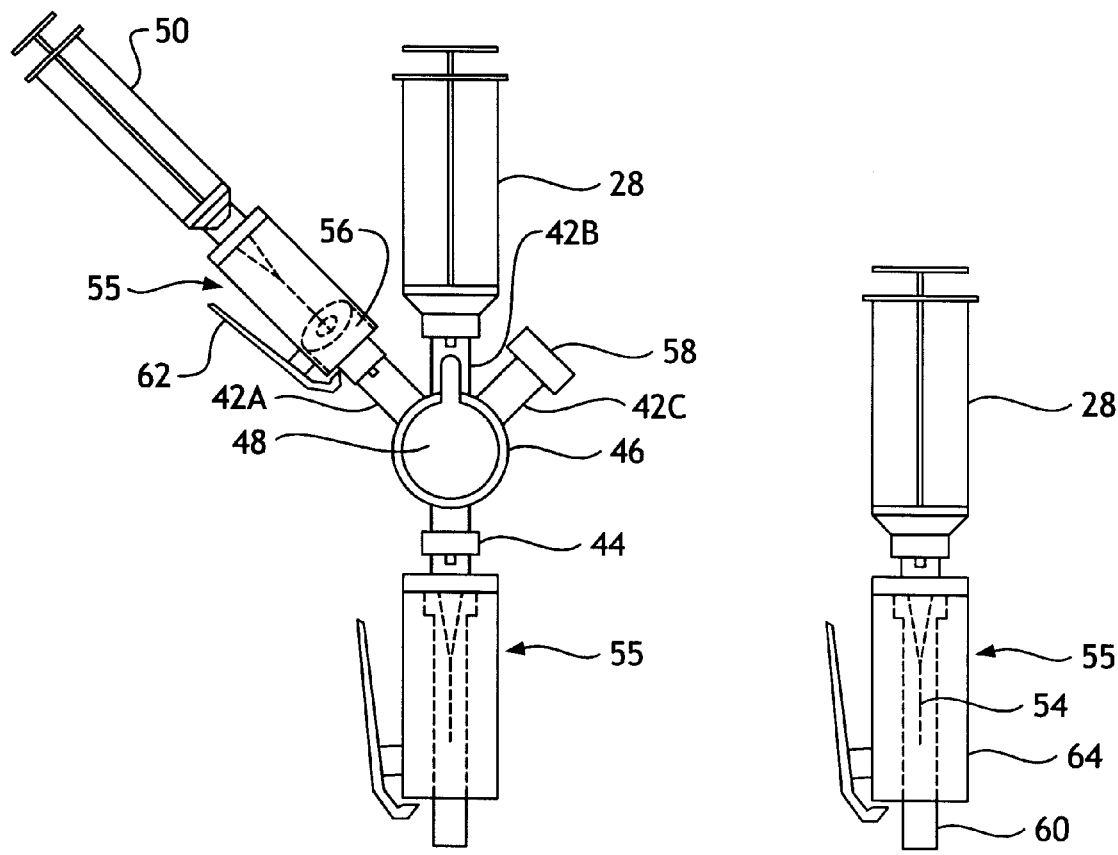
FIG. 8 shows how the blood collecting kit would come packaged for when more than one blood sampling syringe is needed.
Figure 9A:
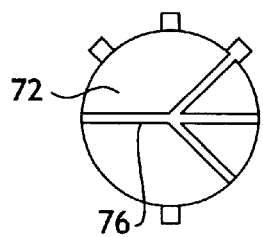
FIGS. 9A–9F show the preferred embodiment of the inside of the blood collecting kit's stopcock and its positions.
Figure 9B:
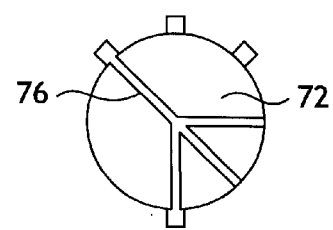
Figure 9C:
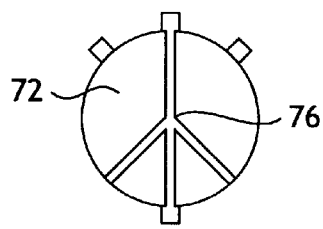
Figure 9D:
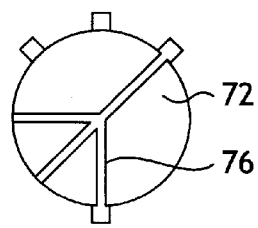
Figure 9E:
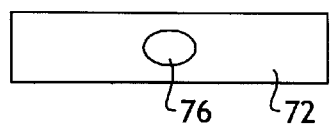
Figure 9F:
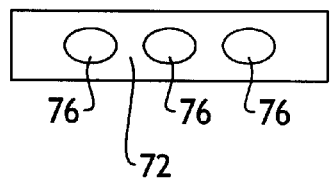
Figure 10A:
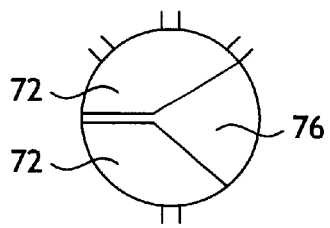
FIGS. 10A–10F show another embodiment of the inside of the current invention's stopcock and its positions.
Figure 10B:
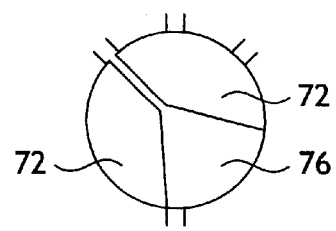
Figure 10C:
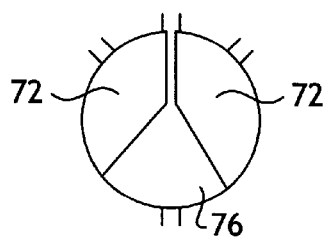
Figure 10D:
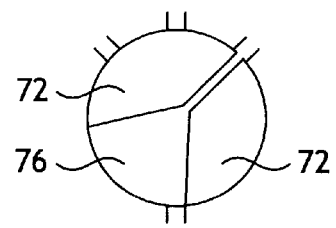
Figure 10E:
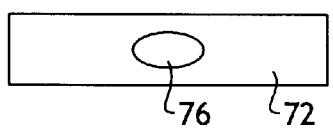
Figure 10F:
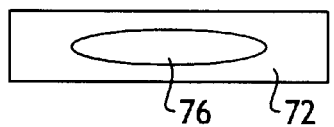

FIGS. 8 and 9—Additional Embodiments

The blood collecting kit can be used to draw additional labs if needed. To achieve this, the kit would come in three separate setups in different sterile packages. This way, the person performing the blood sampling would choose the kit appropriate for the labs needed. The operation of all the kits is the same.

One kit is just for drawing arterial blood gases and is shown in FIGS. 4–7. This kit requires a 1 cc heparinized syringe for the blood sample and would be used most often.

Another kit is for drawing an arterial blood gas and additional labs so it requires a 1 cc heparinized syringe and an empty 3 cc syringe as sample collectors. Please see FIG. 8 which shows how this kit would come packaged. An empty 3 cc syringe is required for additional labs because heparin in the syringe would skew the lab results. Notice with this kit the 1 cc heparinized syringe is attached to female port 42A with a locking access device and matching sample site. This allows for changing the syringes during blood sampling without allowing blood to escape from female port 42A and without risking contamination of the equipment. After blood is obtained for the arterial blood gas, the 1 cc syringe is removed and the 3 cc syringe with the locking access device is placed onto a sample site 56 of the kit. Blood is obtained for the additional labs, then the rest of the steps continue as previously described.

Another kit is for drawing labs other than an arterial blood gas. This kit is set up just like FIG. 4 except it has an empty 3 cc syringe in place of the 1 cc heparinized syringe on female port 42A. This kit would be the least used because arterial blood gases are done very frequently and additional labs are coordinated with the arterial blood gases. Arterial blood gases may eventually be read without removing blood from the line. Then this kit would be used most often.

The preferred embodiment of the inside of the kit's stopcock and its positions is shown in FIGS. 9A–9F. This is the preferred embodiment because it has the smallest passages for fluid flow. A hard plastic 72 rotates in the center of the kit's stopcock when the lever on the outside is manipulated. A hollow passage 76 is where the fluids flow to or from the selected port. This is the preferred embodiment because less fluid is needed to bring whole blood to the sampling port and less flush is needed to clear the line for blood sampling. Note the hollow passage does not have to, and should not be as large as the female ports of the kit.

FIGS. 10A–10F and 11A–11D—Alternative Embodiments

FIGS. 10A–10F show an alternative embodiment of the inside of the blood collecting kit's stopcock and its different positions. A hard plastic 72 rotates in the center of the kit's stopcock when the dial on the outside is manipulated. A hollow passage 76 is where the fluids flow to or from the selected port.

FIGS. 11A–11D show another possible embodiment of the inside of the blood collecting kit's stopcock and its positions. A firm moveable plastic 72 holds a flexible tube 74. A hollow passage 76 of the flexible tubing is where the fluids flow to or from the selected port. Hard plastic stops 78 prevent the inside moving parts from "injuring" the flexible tubing.

Conclusion, Ramifications, and Scope

Thus the reader will see that the arterial blood collecting kit provides a compact, easy to use device that greatly decreases the chance of contamination of a patient's blood. The blood collecting kit is removed from the sampling port after each blood draw, so there is no additional clutter on a neonate's small bed.

Furthermore, the blood collecting kit has the additional advantages in that:

- it provides a method for blood sampling in which the stopcocks and syringes to be manipulated are in close proximity to one another.
- it provides a method for blood sampling in which blood can not flow out of the sampling port when the kit is attached or removed.
- it provides a method for blood sampling in which the stopcocks can not become confused causing blood mixed with infusing fluids to be drawn into the blood sampling syringe.
- it provides an apparatus for blood sampling in which the risk of contamination is almost entirely eliminated, yet requires animal amounts of blood to be taken out of a neonate to bring the whole blood to the sampling port.
- it provides an apparatus that uses the minimal amount of flush to clear the line after blood sampling because the kit is compact.
- it provides an apparatus with the smallest syringe possible used as a flush syringe so as to know exactly how much flush was used.
- it provides a sterile apparatus which uses a fresh flush with each blood drawing procedure.
- it provides an apparatus for blood sampling which eliminates the risk of air being introduced into the line because the syringes are never in communication with one another.
- it provides an apparatus which can be fit onto any female port of a patient's central or arterial line.
- it provides an apparatus that will not be wasted on a blood pressure transducing line if it is not needed.
- it provides an apparatus for drawing arterial blood gases and additional labs if needed without compromising the integrity of the system and then risking contamination.

While my above description contains many specificities, these should not be construed as limitations on the scope of the invention, but rather as an exemplification of one preferred embodiment thereof. Many other variations are possible.

For example, two female ports could come off the top of the kit's stopcock. One port is for the blood sampling syringe. The other port is for a combined blood and infusing fluid aspirating and flush syringe. Then the lever on the kit's stopcock would only change position twice during a blood drawing procedure.

The stopcock on the central line could be a valve assembly instead. Then when the blood collecting kit is placed onto the sample site the flow of infusing fluids is automatically turned off and the path is open between the blood collecting kit and the central line. When the kit is removed, the path would automatically open again between the central line and the infusing fluids.

The kit's stopcock could come in a variety of shapes with many different types of levers. It could be, but is not limited to, that the syringes come off the top of the stopcock like an inverted tripod. The port selecting dial could then be like a collar on the neck of the kit's body just above the male adapter.

The inside of the kit's stopcock could also be changed. It could be made of different materials than plastic, Silastic, etc.

The blood collecting kit can easily be modified for use in pediatric and adult ICUs by making the syringes larger as needed. The kit could be used to obtain blood from any central line on a pediatric or adult patient. The kit could be used to draw any bodily fluids from any central line that can be aspirated on.

The syringes with locking access devices for drawing additional labs could also come packaged separately in different sizes. This way the appropriate size of syringe is chosen for the amount of blood needed at the time of the blood draw.

The syringes on female ports 42A–42C could come in many different sizes and order in regards to one another. Also, the female ports 42A–42C could come at different angles to one another than previously described.

The body of the stopcock can come in different sizes as appropriate.

As stated before, there are many types of locking access devices with matching access ports that could be used with the blood collecting kit.

Reference

*Handbook of Neonatal Intensive Care,* Merenstein, G. B. and Gardner, S. L., $4^{th}$ edition, Mosby, 1998.

What is claimed is:

1. A blood sampling kit for obtaining at least one blood sample from a central line comprising:
    a) a first syringe obtaining said at least one blood sample;
    b) a second blood and infusing fluid aspirating syringe;
    c) a third flush-filled syringe;
    d) a four-way stopcock assembly coupled to each of said first, second and third syringes, the stopcock assembly including a selection device for selecting which of the syringes is allowed to transfer blood or fluid through the stopcock assembly;
    e) an access device coupled to stopcock assembly, the access device assisting in the transfer of fluid or blood to or from the blood sampling kit and the central line, the access device including a needle or blunt cannula assisting in the transfer of fluid or blood, a shroud that surrounds and protects the needle or the blunt cannula, and a fastening device for securing the blood sampling kit.

2. The blood sampling kit of claim 1 wherein the first syringe is about a 1 cc syringe, the second syringe is about a 3 cc syringe, and the third syringe is about a 3 cc syringe.

3. The blood sampling kit of claim 2 wherein the access device is connected to a male adapter and wherein the access device has a sample site.

4. The blood sampling kit of claim 3 wherein at least one stopcock cap is provided to protect and maintain sterilization of at least one port on said four-way stopcock assembly.

5. The blood sampling kit of claim 4 wherein at least one access device cap is provided to protect and maintain sterilization of the access device.

6. A method of sampling blood from a patient comprising the steps of:
    a) cleaning an access port on a central line;
    b) attaching a blood sampling kit to the sample site said sampling kit having at least a first, a second and a third syringe connected thereto;
    c) preventing infusing fluids from being infused into the central line;
    d) positioning a valve assembly to connect a first syringe to the central line fluid flow through an access device;

e) aspirating blood and infusing fluids from the first syringe to bring whole blood to the access port;

f) positioning the valve assembly to connect a second syringe to the central line fluid flow through the access device;

g) aspirating whole blood from the second syringe for the blood sample;

h) positioning the valve assembly to connect the first syringe to the central line fluid flow through the access port;

i) returning the blood mixed with infusing fluids from the first syringe back to the patient;

j) positioning the valve assembly to connect a third syringe to the central line fluid flow through the access device;

k) flushing the central line from the third syringe until it is substantially clear of blood;

l) preventing any further fluid transfer from the sample site; and m) removing the blood collection kit from the sample site.

7. The method of claim 6 wherein the sample site is near the central line.

8. The method of claim 7 wherein the central line is an arterial line.

9. A blood sampling kit for obtaining at least one blood sample from a central line comprising:

a) at least a first, a second, and a third syringe;

b) a valve assembly coupled to each of said first, second and third syringes, the valve assembly including a selection device for selecting which of the syringes is allowed to transfer blood or fluid through the valve assembly;

c) an access device coupled to the valve assembly, the access device assisting in the transfer of fluid or blood to or from sampling kit and the central line.

10. The blood sampling kit of claim 9 wherein the first syringe is about a 1 cc syringe, the second syringe is about a 3 cc syringe, and the third syringe is about a 3 cc syringe.

11. The blood sampling kit of claim 10 wherein the access device is connected to a male adapter and wherein the access device has a sample site.

12. The blood sampling kit of claim 11 wherein at least one valve cap is provided to protect and maintain sterilization of at least one port on said valve assembly.

13. The blood sampling kit of claim 12 wherein at least on access device cap is provided to protect and maintain sterilization of the access device.

14. The blood sampling kit of claim 9 wherein the first syringe is a blood sample syringe, the second syringe is a blood and infusing fluid aspirating syringe, and the third syringe is a flush-filled syringe.

15. The blood sampling kit of claim 9 wherein the value assembly is a stopcock assembly.

16. The blood sampling kit of claim 9 wherein the valve assembly is a four-way stopcock assembly.

* * * * *

UNITED STATES PATENT AND TRADEMARK OFFICE
CERTIFICATE OF CORRECTION

PATENT NO.    : 6,287,265 B1
DATED         : September 11, 2001
INVENTOR(S)   : Cindy L. Gleason It is certified that error appears in the above-identified patent and that said Letters Patent is hereby corrected as shown below:

Column 4,
Line 47, "kdt" should be -- kit --;

Column 9,
Line 22, "animal" should be -- minimal --.

Signed and Sealed this

Second Day of April, 2002

Attest:

JAMES E. ROGAN
*Attesting Officer*  *Director of the United States Patent and Trademark Office*